US012721631B2

(12) United States Patent
Yang et al.

(10) Patent No.: US 12,721,631 B2
(45) Date of Patent: Sep. 1, 2026

(54) HEMOSTATIC CLIP

(71) Applicants: MICROPORT UROCARE (JIAXING) CO., LTD., Jiaxing (CN); MICROPORT UROCARE (SHANGHAI) CO., LTD., Shanghai (CN)

(72) Inventors: Xuefeng Yang, Shanghai (CN); Lu Jiang, Shanghai (CN); Zhen Wang, Shanghai (CN); Quanbin Wang, Shanghai (CN)

(73) Assignees: MICROPORT UROCARE (JIAXING) CO., LTD., Jiaxing (CN); MICROPORT UROCARE (SHANGHAI) CO., LTD., Shanghai (CN)

( * ) Notice: Subject to any disclaimer, the term of this patent is extended or adjusted under 35 U.S.C. 154(b) by 549 days.

(21) Appl. No.: 18/251,668

(22) PCT Filed: Oct. 22, 2021

(86) PCT No.: PCT/CN2021/125598

§ 371 (c)(1),
(2) Date: May 3, 2023

(87) PCT Pub. No.: WO2022/095724

PCT Pub. Date: May 12, 2022

(65) Prior Publication Data

US 2024/0008877 A1 Jan. 11, 2024

(30) Foreign Application Priority Data

Nov. 6, 2020 (CN) ......................... 202011232996.0

(51) Int. Cl.
*A61B 17/122* (2006.01)
*A61B 17/12* (2006.01)

(52) U.S. Cl.
CPC .................... *A61B 17/1227* (2013.01); *A61B 2017/12004* (2013.01)

(58) Field of Classification Search
CPC ...... A61B 17/1227; A61B 2017/12004; A61B 17/10; A61B 17/083; A61B 17/1285;
(Continued)

(56) References Cited

U.S. PATENT DOCUMENTS

2005/0107809 A1* 5/2005 Litscher ............ A61B 17/1285 606/142
2008/0140089 A1* 6/2008 Kogiso ............. A61B 17/1285 606/142
(Continued)

FOREIGN PATENT DOCUMENTS

CN 103930051 A 7/2014
CN 104546055 A 4/2015
(Continued)

*Primary Examiner* — Kathleen S Holwerda
*Assistant Examiner* — James R McGinnity
(74) *Attorney, Agent, or Firm* — MUNCY, GEISSLER, OLDS & LOWE, P.C.

(57) ABSTRACT

A hemostatic clip includes a traction device, a clamping device and a first limiting member. The traction device includes a traction mechanism and a separation mechanism. The clamping device includes a constricting sleeve and a clip head assembly. A proximal end portions of the clip head assembly is inserted in an inner bore of the traction mechanism in an interference-fit manner. The separation mechanism prevents a second locking member of the clip head assembly from being connected to a first locking member of the constricting sleeve, thereby allowing the traction mechanism to drive, under the action of an external force, the clip head assembly to move along an axis of the constricting sleeve. The clip head assembly can be separated from the
(Continued)

traction mechanism simply by providing an external force that can overcome the interference fit between the two.

13 Claims, 7 Drawing Sheets

(58) Field of Classification Search
CPC ........ A61B 17/122; A61B 2017/00296; A61B 2017/2944; A61B 17/29; A61B 17/0487; A61B 17/12
See application file for complete search history.

(56) References Cited

U.S. PATENT DOCUMENTS

| | | | | |
|---|---|---|---|---|
| 2018/0153552 | A1* | 6/2018 | King | A61B 17/128 |
| 2018/0344323 | A1 | 12/2018 | Shi | |
| 2020/0113573 | A1 | 4/2020 | Shi | |
| 2020/0146686 | A1* | 5/2020 | Haack | A61B 17/1285 |
| 2020/0155159 | A1* | 5/2020 | Murray | A61B 17/122 |
| 2021/0290244 | A1* | 9/2021 | Fujimoto | A61B 17/1222 |
| 2023/0172442 | A1* | 6/2023 | Tsuneto | A61B 1/018<br>604/19 |

FOREIGN PATENT DOCUMENTS

| | | | |
|---|---|---|---|
| CN | 205322412 | U | 6/2016 |
| CN | 110393564 | A | 11/2019 |
| CN | 214104517 | U | 9/2021 |
| WO | WO2019205332 | A1 | 10/2019 |

* cited by examiner

HEMOSTATIC CLIP

TECHNICAL FIELD

The present invention relates to medical devices and, in particular, to a hemostatic clip.

BACKGROUND

With the continuous development of endoscopic minimally invasive surgery, various endoscopic surgical procedures, including endoscopic submucosal dissection (ESD), endoscopic retrograde cholangiopancreatography (ERCP) and natural orifice transluminal endoscopic surgery (NOTES), are widely used. For these endoscopic minimally invasive procedures, safe and effective intraoperative closure of defects or perforations in digestive tissue is a critical issue that must be addressed.

Hemostatic clips are instruments for closing defects or perforations in luminal tissue. Existing hemostatic clips have openable-and-closable and rotatably clip heads. After being delivered to a target site, such a clip head is activated by a traction mechanism to open, close and/or rotate, as desired, to clamp tissue at the target site to close a defect or perforation there. After that, the clip head is separated from the traction mechanism and remains in the patient's body until it falls off and is passed out of the body through the gastrointestinal tract after the defect or perforation is closed as a result of tissue growth at the target site.

In the existing hemostatic clips, the clip head can be coupled to the traction mechanism by a hook, and the coupling can be destroyed by breaking the hook. However, if the broken hook falls onto a wound, it may cause inflammation and other issues. Alternatively, the clip head may be coupled to the traction mechanism by a ball head and a mating connecting yoke and decoupled therefrom by causing deformation of the connecting yoke. However, the fabrication of the connecting yoke involves a complicated process.

SUMMARY OF THE INVENTION

It is an objective of the present invention to provide a hemostatic clip, which has a simpler structure and does not have the risk of a broken portion remaining in a patient' body during its use.

To this end, the present invention provides a hemostatic clip, including:

a traction device including a traction mechanism and a separation mechanism, the traction mechanism defining an inner bore at a distal end thereof, the separation mechanism disposed outside of the inner bore at a distal end thereof;

a clamping device including a constricting sleeve and a clip head assembly, the constricting sleeve provided thereon with a first locking member, the clip head assembly partially disposed within the constricting sleeve, the clip head assembly including a clip arm and an engagement member, the clip arm disposed on the engagement member, the clip arm provided at a proximal end thereof with a second locking member for connection with the first locking member, wherein a proximal end portion of the engagement member is inserted in the inner bore so as to form an interference fit with the inner bore, and wherein the separation mechanism prevents the second locking member from being connected to the first locking member, thereby allowing the traction mechanism to drive, under the action of an external force, the clip head assembly to move along an axis of the constricting sleeve to switch the clip head assembly between a closed configuration and an opened configuration; and a first limiting member for defining a maximum distance that the clip head assembly is movable toward a proximal end of the constricting sleeve, wherein the hemostatic clip is configured so that, in the closed configuration of the clip head assembly, when the first limiting member prevents further movement of the clip head assembly toward the proximal end of the constricting sleeve and when a pulling force greater than a first predetermined value is applied to the traction mechanism, the proximal end portion of the engagement member is disengaged from the inner bore, and the separation mechanism does not confine a proximal end portion of the clip arm any longer, allowing the second locking member to be connected to the first locking member.

Optionally, the separation mechanism may include two first stop walls, which extend along an axis of the traction mechanism and are arranged in circumferential symmetry with respect to the inner bore and configured to confine the proximal end portion of the clip arm on internal sides of the first stop walls, thereby preventing the second locking member from being connected to the first locking member.

Optionally, the clamping device may further include a second limiting member, which is provided on the constricting sleeve on a distal side of the engagement member and is configured to define a maximum distance that the clip head assembly is movable away from the proximal end of the constricting sleeve, thereby preventing the clip head assembly from distal dislodgement from the constricting sleeve.

Optionally, the first locking member may include a locking slot provided in a tubular wall of the constricting sleeve, and the second locking member may include a stop block, wherein the second limiting member is also configured to limit circumferential relative positions of the clip head assembly and the constricting sleeve to enable the stop block to enter and engage with the locking slot after the confinement is removed.

Optionally, the second limiting member may extend radially with respect to the constricting sleeve and delimit two channels together with the tubular wall of the constricting sleeve, wherein two clip arms are provided so as to protrude through the respective channels out of the constricting sleeve from the distal end thereof.

Optionally, the second limiting member may include a pin, which, for example, connected at opposing axial ends thereof to the tubular wall of the constricting sleeve. Alternatively, the second limiting member may include two second stop walls provided in circumferential symmetry at the distal end of the constricting sleeve.

Optionally, the hemostatic clip may further include an adaptor bush assembly, which is detachably coupled to the proximal end of the constricting sleeve so as to communicate with the constricting sleeve and configured to be rotatable relative to the constricting sleeve, wherein the traction device is partially disposed in the adaptor bush assembly so as to be movable along an axis of the adaptor bush assembly, and wherein the hemostatic clip is configured so that the traction mechanism is able to drive, under the action of an external force, rotation of the clip head assembly about an axis of the traction mechanism and rotation of the constricting sleeve about its own axis.

Optionally, the first limiting member may include a first limiting surface and a second limiting surface, the first limiting surface provided on the engagement member and configured to abut against the second limiting surface, wherein a first step surface is defined on an outer wall surface of the constricting sleeve, and the second limiting surface is formed on an inner wall surface of the constricting sleeve, wherein the constricting sleeve is further provided therein with a first connecting slot located proximally with respect to the first step surface and the second limiting surface, wherein the hemostatic clip further includes an elastic connecting member, the elastic connecting member including a base portion and a shaft portion, the base portion disposed within the adaptor bush assembly and provided therein with a through hole for passage of the traction mechanism therethrough, the shaft portion disposed on a side of the base portion closer to a distal end of the adaptor bush assembly so as to extend along the axis of the adaptor bush assembly, the shaft portion defining a bent fin at a distal end thereof, the bent fin passing through the first connecting slot and protruding out of the constricting sleeve, wherein the adaptor bush assembly defines an inwardly-projecting third limiting member at the distal end thereof, and wherein the adaptor bush assembly is disposed at the distal end thereof over the outer surface of the constricting sleeve around the proximal end of the constricting sleeve so that the third limiting member is confined between the bent fin and the first step surface.

Optionally, the first limiting member may include a first limiting surface and a second limiting surface, the first limiting surface provided on the engagement member and configured to abut against the second limiting surface, wherein a second step surface is defined on an outer wall surface of the adaptor bush assembly around a distal end thereof, wherein the adaptor bush assembly is provided therein with a second connecting slot located distally with respect to the second step surface, wherein the hemostatic clip further includes an elastic connecting member, the elastic connecting member including a base portion and a shaft portion, the base portion disposed within the adaptor bush assembly and provided therein with a through hole for passage of the traction mechanism therethrough, the shaft portion disposed on a side of the base portion closer to a distal end of the adaptor bush assembly so as to extend along the axis of the adaptor bush assembly, the shaft portion defining a bent fin at a distal end thereof, the bent fin passing through the second connecting slot and protruding out of the adaptor bush assembly, wherein the constricting sleeve defines an inwardly-projecting fourth limiting member at the proximal end thereof, and wherein the constricting sleeve is disposed at the proximal end thereof over the outer surface of the adaptor bush assembly around the distal end of the adaptor bush assembly so that the fourth limiting member is confined between the bent fin and the second step surface and that a distal end face of the adaptor bush assembly makes up the second limiting surface for abutting against the first limiting surface.

Optionally, the traction mechanism may include a core wire and a coupling tube, the core wire passed through the through hole in the base portion, the coupling tube disposed at a distal end of the core wire, the coupling tube defining the inner bore, the coupling tube having an outer diameter at a proximal end thereof that is greater than a diameter of the through hole, wherein the hemostatic clip is configured so that, after the proximal end portion of the engagement member is disengaged from the inner bore, when the proximal end of the coupling tube abuts against the base portion and when a pulling force greater than a second predetermined value is applied to the traction mechanism, the bent fin deforms so that the adaptor bush assembly is separated from the constricting sleeve.

Optionally, the hemostatic clip may further include a handle assembly, the handle assembly including a grip member, a slidable member and a rotatable member, the grip member defining an axially-extending slide slot, the slidable member disposed in the slide slot so as to be slidable therein, the rotatable member rotatably disposed at a distal end of the grip member, wherein the traction mechanism proximally extends out of the adaptor bush assembly from a proximal end thereof into the handle assembly and is connected to both the slidable member and the rotatable member in the handle assembly, and wherein the hemostatic clip is configured so that the slidable member drives, when sliding in the slide slot, the traction mechanism to move along the axis of the adaptor bush assembly to cause the clip head assembly to move along the axis of the constricting sleeve and that the rotatable member drives, when rotating relative to the grip member, the traction mechanism to rotate about its own axis to cause rotation of the clip head assembly and the constricting sleeve.

Optionally, the traction mechanism may include a core wire, a coupling tube, a first connecting block and a second connecting block, the coupling tube disposed at a distal end of the core wire and defining the inner bore, the first connecting block and the second connecting block both disposed over the core wire around a proximal end thereof, the second connecting block located proximally with respect to the first connecting block, the first connecting block coupled to the rotatable member and configured to be rotatable in synchronization with the rotatable member and axially movable relative to the rotatable member, the second connecting block coupled to the slidable member and configured to be axially stationary relative to the slidable member and circumferentially rotatable relative to the slidable member.

Alternatively or additionally, the adaptor bush assembly may include a sleeve and a spring tube, which are axially connected to each other, the sleeve connected at a distal end thereof to the proximal end of the constricting sleeve, the spring tube provided at a proximal end thereof with a locating tube, the locating tube located distally with respect to the first connecting block, the locating tube coupled to the rotatable member in the handle assembly, the locating tube configured to be axially stationary relative to the rotatable member and circumferentially rotatable relative to the rotatable member.

The hemostatic clip of the present invention has the following advantages over the prior art:

It includes a traction device, a clamping device and a first limiting member. The traction device includes a traction mechanism and a separation mechanism. The traction mechanism defines an inner bore at a distal end thereof, and the separation mechanism is disposed outside of the inner bore at a distal end thereof. The clamping device includes a constricting sleeve and a clip head assembly. The constricting sleeve is provided thereon with a first locking member, and the clip head assembly is partially disposed within the constricting sleeve and includes a clip arm and an engagement member. The clip arm is disposed on the engagement member and provided at a proximal end thereof with a second locking member for connection with the first locking member. A proximal end portion of the engagement member is inserted in the inner bore so as to form an interference fit with the inner bore, and the separation mechanism prevents the second locking member from being connected to the first locking member, thereby allowing the traction mechanism to drive, under the action of an external force, the clip head assembly to move along an axis of the constricting sleeve to switch the clip head assembly between a closed configuration and an opened configuration. The first limiting member is configured to define a maximum distance that the clip head assembly is movable toward a proximal end of the constricting sleeve. The hemostatic clip is configured so that, in the closed configuration of the clip head assembly, when the first limiting member prevents further movement of the clip head assembly toward the proximal end of the constricting sleeve and when a pulling force greater than a first predetermined value is applied to the traction mechanism, the proximal end portion of the engagement member is disengaged from the inner bore, and the separation mechanism does not confine a proximal end portion of the clip arm any longer, allowing the second locking member to be connected to the first locking member. The interference fit established between the engagement member and the inner bore enables a simple structure and can be eliminated simply by applying a pulling force that can overcome the interference fit, without involving the breakage of any structural component, thereby avoiding the risk of a broken portion remaining in a patient's body and possibly accessing a wound and providing increased safety and enhanced reliability. In particular, with the proximal end portion of the clip arm being confined in the separation mechanism, the clip head assembly is able to reciprocate along the axis of the constricting sleeve to apply repeated positional and orientational adjustments to the clip head assembly to allow the hemostatic clip to better clamp target tissue.

BRIEF DESCRIPTION OF THE DRAWINGS

The accompanying drawings are provided to facilitate a better understanding of the present invention and do not unduly limit the scope thereof in any sense, in which:

FIG. 5 is in a different plane from that of FIG. 4, in which a pin and an elastic connecting member are not shown;

FIG. 15 is in a different plane from that of FIG. 14, in which an elastic connecting member is not shown.

DETAILED DESCRIPTION

Figure 1:
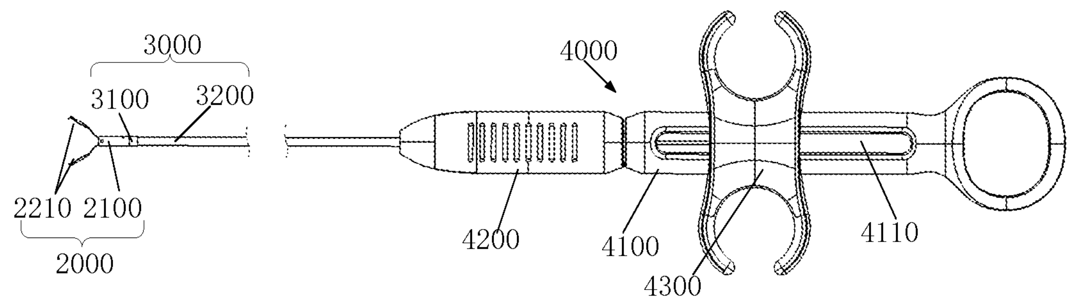
FIG. 1 is a schematic diagram showing the structure of a hemostatic clip according to a first embodiment of the present invention, in which a clip head assembly is in an opened configuration.

Particular embodiments of the present invention will be described below by way of specific examples. Based on the disclosure and teachings provided herein, a person of ordinary skill in the art will readily realize other advantages and benefits provided by the present invention. The present invention may also be otherwise embodied or applied through different embodiments, and various modifications or changes may be made to the details disclosed herein from different points of view or for different applications, without departing from the spirit of the present invention. It should be noted that the accompanying drawings are provided herein merely to schematically illustrate the basic concept of the present invention. Accordingly, they only show components relating to the present invention but not necessarily depict all the components as well as their real shapes and dimensions in practical implementations. In practice, the configurations, counts and relative scales of the components may vary arbitrarily and their arrangements may be more complicated.

In the following, each of the embodiments is described as having one or more technical features. However, this does not mean that the present invention must be practiced necessarily with all such technical features, or separately with some or all the technical features in any of the embodiments. In other words, as long as the present invention can be put into practice, a person skilled in the art may choose some or all of the technical features in any of the embodiments or combine some or all of the technical features in different embodiments based on the teachings herein and depending on relevant design specifications or the requirements of practical applications. In this way, the present invention can be carried out more flexibly.

As used herein, the singular forms “a”, “an” and “the” include plural referents, and the plural form “a plurality of” means “two or more”, unless the context clearly dictates otherwise. As used herein, the term “or” is generally employed in the sense including “and/or” unless the context clearly dictates otherwise. The terms “mounting”, “coupling” and “connection” should be interpreted in a broad sense. For example, a connection may be a permanent, detachable or integral connection, or a mechanical or electrical connection, or a direct or indirect connection with one or more intervening media, or an internal communication or interaction between two elements. Those of ordinary skill in the art can understand the specific meanings of the above-mentioned terms herein, depending on their context.

Objectives, features and advantages of the present invention will become more apparent upon reading the following more detailed description of the present invention, which is set forth by way of particular embodiments with reference to the accompanying drawings. Note that the figures are provided in a very simplified form not necessarily drawn to exact scale and for the only purpose of facilitating easy and clear description of the embodiments. In the drawings, like reference numbers indicate identical or similar elements. Like numerals indicate like elements throughout the several views.

As used herein, the terms “proximal” and “distal” are intended to refer to relative orientations, relative positions and directions between components of a medical device or actions thereof, as viewed by a physician operating the device. Without wishing to be limiting, a “proximal end” usually refers to an end closer to the operator, and a “distal end” to an end first enters the body of a patient, during normal operation of the medical device.

Embodiment 1

Referring to FIGS. 1 to 6, in a first embodiment of the present invention, there is provided a hemostatic clip including a traction device, a clamping device and a first limiting member. The traction device includes a traction mechanism 1100 and a separation mechanism. The distal end of the traction mechanism 1100 defines an inner bore 1101. In this embodiment, the separation mechanism preferably includes a first stop wall 1200, the first stop wall 1200 is disposed outside of the distal end of the inner bore 1101 and extends along an axis of the traction mechanism 1100. The clamping device includes a constricting sleeve 2100 and a clip head assembly 2200. The constricting sleeve 2100 is provided thereon with a first locking member. The clip head assembly 2200 is partially received in the constricting sleeve 2100 and includes clip arms 2210 and an engagement member 2220. The clip arms 2210 are provided on the engagement member 2220, a proximal end of the clip arms 2210 is provided with second locking members for connection with the first locking member. A proximal end portion of the engagement member 2220 is inserted in the inner bore 1101 so as to form an interference fit with the inner bore 1101. Moreover, a proximal end of the clip arms 2210 are confined on an internal side of the first stop wall 1200, preventing the second locking members from being connected to the first locking member. As a result, the traction mechanism 1100 is allowed to drive, under the action of an external force, the clip head assembly 2200 to move along the axis of the constricting sleeve 2100 to switch the clip head assembly 2200 between a closed configuration and an opened configuration. The first limiting member is configured to define a maximum distance that the clip head assembly 2200 can move toward a proximal end of the constricting sleeve 2100.

It is to be noted that the extension of the first stop wall 1200 along the axis of the traction mechanism 1100 includes both extension of the first stop wall 1200 in parallel to the axis of the traction mechanism 1100 and extension of the first stop wall 1200 in a direction forming such an angle with the axis of the traction mechanism 1100 that the proximal end of the clip arms 2210 can be confined on the internal side of the first stop wall 1200. Here, the “internal side” refers to the side of the first stop wall 1200 closer to the axis of the traction mechanism 1100. Through confining the proximal end of the clip arms 2210 on the internal side of the first stop wall 1200, the second locking members are separated from the first locking member, and the two are prevented from being connected to each other.

It would be appreciated that two clip arms 2210 may be included. In order to clamp target tissue in a patient’s body with the hemostatic clip, an operator may apply a pulling force to a proximal end of the traction mechanism 1100 to cause movement of the clip head assembly 2200 toward the proximal end of the constricting sleeve 2100. As a result, a tubular wall of the constricting sleeve 2100 will press the clip arms 2210, causing the distal ends of the two clip arms 2210 approach each other. In this way, the clip head assembly 2200 can be switched to the closed configuration. On the contrary, a pushing force applied by the operator to the traction mechanism 1100 may cause movement of the clip head assembly 2200 away from the proximal end of the constricting sleeve 2100 until the tubular wall of the constricting sleeve 2100 does not press the clip arms 2210 any longer. In this way, the clip head assembly 2200 is switched to the opened configuration. Here, the “pulling force” refers to a force acting in the direction from the distal to proximal end of the constricting sleeve 2100, and the “pushing force” refers to a force acting in the direction from the proximal to distal end of the constricting sleeve 2100. Moreover, the “movement of the clip head assembly 2200 toward the proximal end of the constricting sleeve 2100” refers to movement of the clip head assembly 2200 in the direction from the distal to proximal end of the constricting sleeve 2100, and the “movement of the clip head assembly 2200 away from the proximal end of the constricting sleeve 2100” refers to movement of the clip head assembly 2200 in the direction from the proximal to distal end of the constricting sleeve 2100.

In the closed configuration of the clip head assembly 2200, with the first limiting member stopping further movement of the clip head assembly 2200 toward the proximal end of the constricting sleeve 2100, when the operator applies a pulling force exceeding a first predetermined value to the traction mechanism 1100, the proximal end of the engagement member 2220 will protrude out of the inner bore 1101, and the first stop wall 1200 will no longer constrict the proximal ends of the clip arms 2210. As a result, the second locking members are connected to the first locking member, the clip head assembly 2200 is locked and is maintained in the closed configuration. The "first predetermined value" may be determined as any value depending on the strength of the interference fit established between the proximal end portion of the engagement member 2220 and the inner bore 1101, as long as the interference fit can be overcome by a pulling force exceeding the first predetermined value applied to the traction mechanism 1100.

According to this embodiment, connecting the engagement member 2220 of the clip head assembly 2200 to the traction mechanism 1100 with an interference fit can provide the advantage of a simple structure. Moreover, the connection can be destroyed simply by applying a pulling force to the traction mechanism 1100, which overcomes the interference fit. This offers the advantages of convenience and ease of operation and higher safety of use because it does not involve the breakage of any structural component and thus does not suffer from the problem that a broken portion of the component may remain in the patient's body and possibly access a wound to cause inflammation or other issues.

In this embodiment, the first limiting member includes a first limiting surface and a second limiting surface. The first limiting surface is defined on the engagement member 2220, and the second limiting surface is defined on an inner wall surface of the constricting sleeve 2100 on a proximal side of the first locking member and configured to abut against the first limiting surface.

The clamping device further includes a second limiting member provided on the constricting sleeve 2100 on a distal side of the engagement member 2220. The second limiting member is configured to define a maximum distance that the clip head assembly 2200 can move away from the proximal end of the constricting sleeve 2100, thereby preventing the clip head assembly 2200 from dislodgement from the distal end of the constricting sleeve 2100. Apart from this, the second limiting member is also configured to limit circumferential relative positions of the clip head assembly 2200 and the constricting sleeve 2100 to ensure circumferential alignment and hence successful connection of the second locking members with the first locking member.

In addition, the hemostatic clip further includes an adaptor bush assembly 3000, the adaptor bush assembly 3000 is detachably connected to the proximal end of the constricting sleeve 2100 so as to be brought into communication with the constricting sleeve 2100. The traction device is partially received in the adaptor bush assembly 3000 so as to be movable along an axis of the adaptor bush assembly 3000. By "detachably connected", it is intended to mean that the adaptor bush assembly 3000 can be detached from the constricting sleeve 2100 when a predefined condition is satisfied. Moreover, the constricting sleeve 2100 and the adaptor bush assembly 3000 are rotatable relative to each other. As such, when the traction mechanism 1100 is rotated under the action of an external force, the clip head assembly 2200 and the constricting sleeve 2100 will be driven to rotate in synchronization, facilitating positional adjustment of the clip head assembly 2200 by the operator.

The hemostatic clip further includes a handle assembly 4000 configured to be connected to the proximal end of the traction mechanism 1100 and a proximal end of the adaptor bush assembly 3000. The operator can manipulate the handle assembly 4000 to apply forces to the traction mechanism 1100, thereby activating the clamping device to perform various motions.

The structures of the various components in the hemostatic clip of the present embodiment and how they are assembled together will be described in detail below with reference to the accompanying drawings.

Figure 3:
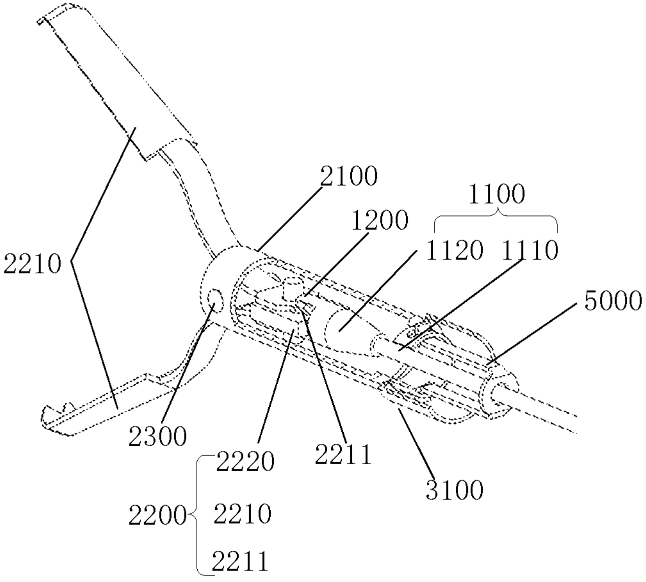
FIG. 3 is a schematic diagram showing the structure of a portion of the hemostatic clip according to the first embodiment of the present invention.
Figure 4:
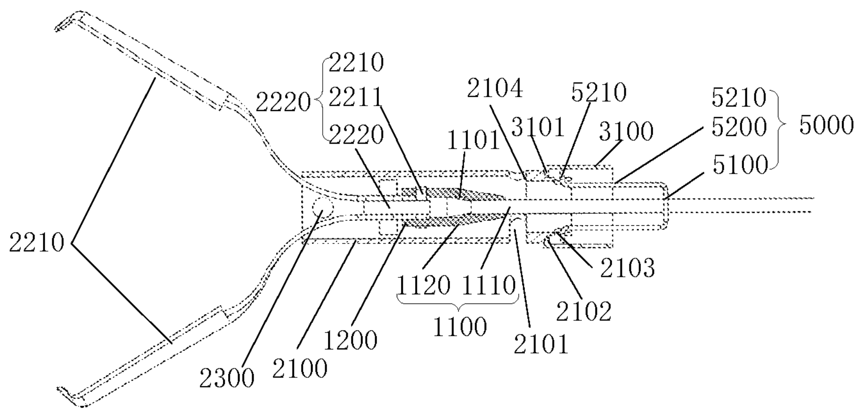
FIG. 4 is a cross-sectional view of a portion of the hemostatic clip according to the first embodiment of the present invention.
Figure 5:
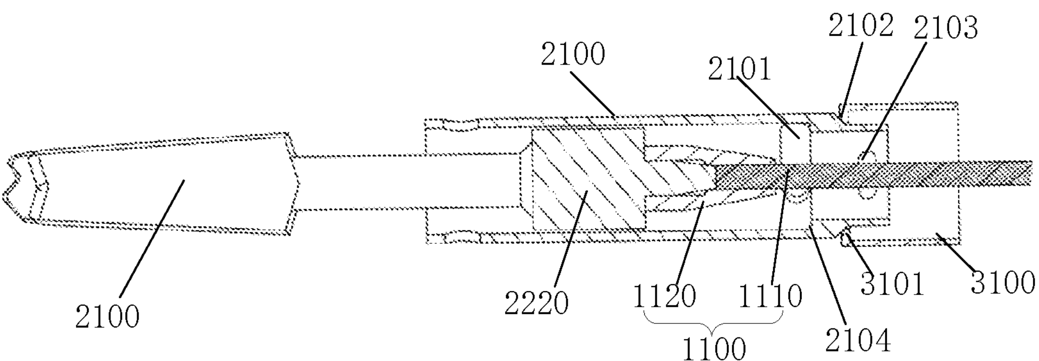
FIG. 5 is a cross-sectional view of a portion of the hemostatic clip according to the first embodiment of the present invention.
Figure 6:
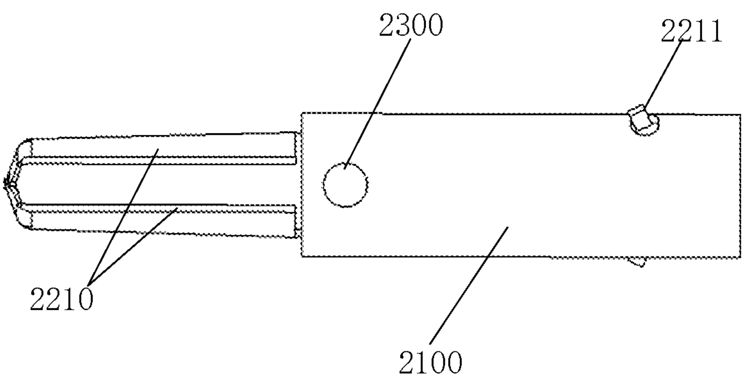
FIG. 6 is a schematic diagram showing the structure a portion of the hemostatic clip according to the first embodiment of the present invention, in which second locking members are coupled to a first locking member.
Figure 7:
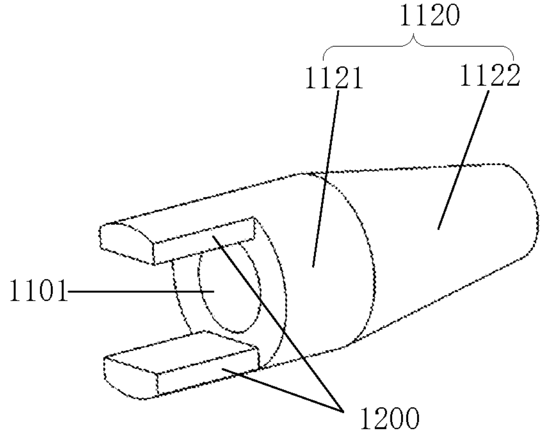
FIG. 7 schematically illustrates how a coupling tube mates with a first stop wall in the hemostatic clip according to the first embodiment of the present invention.

Referring to FIGS. 3 to 5, in conjunction with FIG. 7, the traction mechanism 1100 includes a core wire 1110 and a coupling tube 1120. The coupling tube 1120 is disposed over a distal end portion of the core wire 1110 and defines the inner bore 1101. An outer diameter of the coupling tube 1120 is greater than an outer diameter of the core wire 1110. Preferably, the coupling tube 1120 includes a distal section 1121 and a proximal section 1122. The distal section 1121 is cylindrical, and the proximal section 1122 is tapered, for example frusto-conical, and has a cross-section gradually decreasing in the direction of from its distal to proximal end, facilitating its connection with the core wire 1110. The inner bore 1101 may have a constant inner diameter. Alternatively, the inner bore 1101 may be designed as a stepped bore.

The first stop wall 1200 is disposed on the distal end portion of the coupling tube 1120. In one implementation, two first stop walls 1200 are provided on the coupling tube 1120 in circumferential symmetry. In this case, each first stop wall 1200 is configured to confine a proximal end portion of a respective one of the clip arms 2210 on its internal side.

Figure 8:
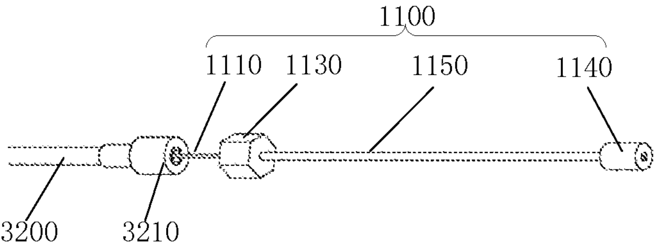
FIG. 8 is a schematic illustration of a portion of the hemostatic clip according to the first embodiment of the present invention, which particularly shows the structure of a proximal end portion of a traction mechanism and the structure of a proximal end portion of an adaptor bush assembly.

Referring to FIG. 8, the traction mechanism 1100 further includes a first connecting block 1130 and a second connecting block 1140, the first connecting block 1130 and the second connecting block 1140 are both on a proximal end of the core wire 1110. The second connecting block 1140 is located proximally with respect to the first connecting block 1130. The first connecting block 1130 has a non-rotating shape. For example, the first connecting block 1130 may have a triangular, quadrilateral, regular hexagonal or other cross-section. The second connecting block 1140 may have a circular cross-section. Both the first connecting block 1130 and the second connecting block 1140 are connected to the handle assembly 4000, as will be described in greater detail below. Preferably, the core wire 1110 includes a core wire body and a core wire jacket wrapped over an outer surface of the core wire body. The core wire jacket is provided to reduce friction that the traction mechanism 1100 encounters during its movement along the axis of the adaptor bush assembly 3000, lowering the probability of bending of the core wire 1110.

The traction mechanism 1100 further includes a reinforcing sleeve 1150 disposed over a portion of the core wire 1100 between the first connecting block 1130 and the second connecting block 1140, the reinforcing sleeve 1150 is connected to both the first connecting block 1130 and the second connecting block 1140 at its opposing axial ends. The reinforcing sleeve 1500 can strengthen the traction mechanism 1100 and reduce its likelihood of bending.

With particular reference to FIGS. 3 to 5, the constricting sleeve 2100 may be a cylindrical structure defining a first lumen axially extending therethrough and configured to receive the clip head assembly 2200 therein. The first locking member includes locking slots 2101 defined in the tubular wall of the constricting sleeve 2100. In this embodiment, the constricting sleeve 2100 includes a first section and a second section. The first section is located distally with respect to the second section. The first section has an outer diameter greater than an outer diameter of the second section. Thus, a first step surface 2102 is defined on an outer wall surface of the constricting sleeve 2100. Preferably, the locking slots 2101 are defined around a proximal end of the first section. First connecting slots 2103 are defined in the second section. That is, the locking slots 2101 are located distally with respect to the first step surface 2102, while the first connecting slots 2103 are located proximally with respect to the first step surface 2102. Both the first step surface 2102 and the first connecting slots 2103 are configured for mating and connection with the adaptor bush assembly 3000, as will be described in greater detail below. A third step surface 2104 is defined on the inner wall surface of the constricting sleeve 2100.

Figure 9:
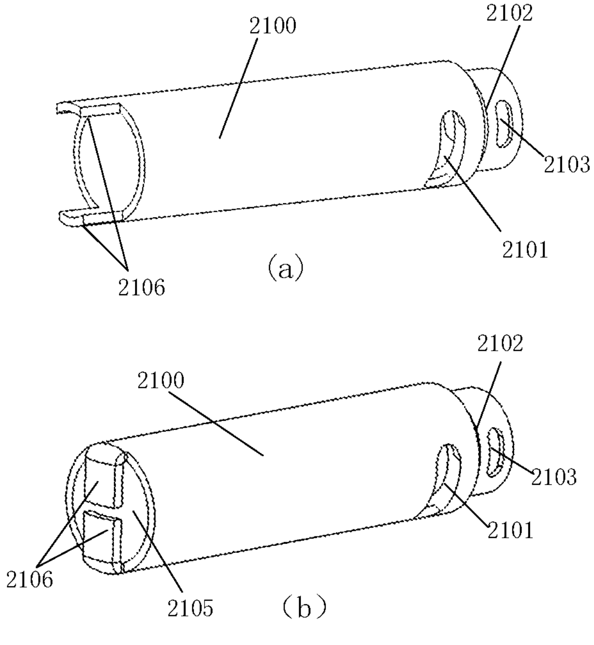
FIG. 9 schematically illustrates how a constricting sleeve mates with a second limiting member in the hemostatic clip according to the first embodiment of the present invention, in which (a) is a schematic illustration before second stop walls are bent; and (b) is a schematic illustration after the second stop walls are bent to form the second limiting member.

The second limiting member is provided at the distal end of the constricting sleeve 2100 and extends radially with respect to the constricting sleeve 2100. The second limiting member delimits two channels 2105 (see FIG. 9(*b*)) along with the tubular wall of the constricting sleeve 2100. In one implementation, as shown in FIGS. 3 to 5, the second limiting member includes a pin 2300, the pin 2300 is connected at its opposing axial ends to the tubular wall of the constricting sleeve 2100, thereby the pin 2300 defining the two separate channels 2105 together with the tubular wall. In another implementation, as shown in FIG. 9, the second limiting member includes two second stop walls 2106 disposed on the distal end portion of the constricting sleeve 2100. The two second stop walls 2106 may be symmetrical and abut against each other. During fabrication, the two second stop walls 2106 may be formed by removing unwanted portions of a single tube. As a result, the other portion of the tube than the second stop walls 2106 serves as the constricting sleeve 2100, while the second stop walls 2106 extend along the axis of the constricting sleeve 2100. After that, forces may be applied to the second stop walls 2106 to bend them inwardly with respect to the constricting sleeve 2100 until they extend radially with respect to the constricting sleeve 2100.

Figure 10:
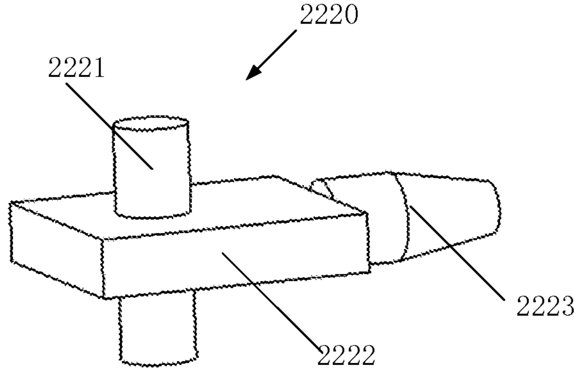
FIG. 10 is a schematic diagram showing the structure of an engagement member according to the first embodiment of the present invention.

FIG. 10 is a schematic diagram showing the structure of the engagement member 2220. As shown in FIG. 10, the engagement member 2220 includes a first connecting shaft 2221, a third connecting block 2222 and a second connecting shaft 2223. The first connecting shaft 2221 and the second connecting shaft 2223 are both connected to the third connecting block 2222, and the first connecting shaft 2221 is perpendicular to the axis of the constricting sleeve 2100. Opposing axial end portions of the first connecting shaft 2221 project from the third connecting block 2222 and are connected to middle portions of the clip arms 2210 (see FIGS. 3 and 4). The third connecting block 2222 may be a block with all rectangular faces, in which a proximal end face is perpendicular to the axis of the constricting sleeve 2100. Of course, in other implementations, the faces of the third connecting block 2222 may be otherwise shaped than rectangular. For example, they may be circular, oval or the like. A distal end of the second connecting shaft 2223 is connected to the third connecting block 2222 so as to extend parallel to the axis of the constricting sleeve 2100. The proximal end of the second connecting shaft 2223 is configured to be inserted into the inner bore 1101 of the traction mechanism 1100 so as to form an interference fit with the inner bore 1101.

As shown in FIGS. 3 and 4, the middle portions of the two clip arms 2210 are connected to the respective opposing axial ends of the first connecting shaft 2221 (e.g., apertures that can mate with the first connecting shaft 2221 may be provided in the middle portions of the clip arms 2210 so that the middle portions of the clip arms 2210 may be disposed over the first connecting shaft 2221 along the axis of the first connecting shaft 2221). In this way, the distal and proximal ends of the clip arms 2210 are both free ends. The clip arms 2210 are configured to be elastic, stop blocks 2211 are provided on the outer surfaces around the proximal ends of the clip arms 2210 to serve as the second locking members. Here, by "free ends", it is intended to mean that the distal and proximal ends of the clip arms 2210 are not secured to any other mechanism. The "outer surfaces" refer to the surfaces of the two clip arms 2210 that face away from each other, i.e., their surfaces facing the inner wall surface of the constricting sleeve 2100 when the clip arms 2210 are assembled to the constricting sleeve 2100.

When the clip head assembly 2200, the constricting sleeve 2100 and the traction device are assembled together, the distal ends of the two clip arms 2210 protrude out of the constricting sleeve 2100 through the respective two channels 2105 at the distal end of the clip head assembly 2200. Moreover, the proximal end of the third connecting shaft 2223 of the engagement member 2220 is inserted into the inner bore 1101 of the traction mechanism 1100, and the proximal end of the two clip arms 2210 are embedded in the internal side of the first stop wall 1200 (i.e., the proximal end of the clip arms 2210 are clamped between the internal side of the first stop wall 1200 and the outer surface of the third connecting shaft 2223). As such, the stop blocks 2211 are separated from the locking slots 2101. In this configuration, before the engagement member 2220 is separated from the traction mechanism 1100, the operator may repeatedly push and pull the traction mechanism 1100 to switch the clip head assembly 2200 between the opened and closed configurations. When the target tissue to be clamped is situated between the two clip arms 2210, the operator may pull the traction mechanism 1100 to cause the clip head assembly 2200 to move toward the proximal end of the constricting sleeve 2100 to clamp the target tissue. Upon the proximal end face of the third connecting block 2222 in the engagement member 2220 coming into abutment against the third step surface 2104 of the constricting sleeve 2100, the clip head assembly 2200 cannot move toward the proximal end of the constricting sleeve 2100 anymore. That is, the proximal end face of the third connecting block 2222 serves as the aforementioned first limiting surface, and the third step surface 2104 of the constricting sleeve 2100 acts as the second limiting surface. The operator may then apply a pulling force greater than the first predetermined value to the traction mechanism 1100 to overcome the interference fit between the engagement member 2220 (more precisely, the second connecting shaft 2223) and the inner bore 1101 to separate the traction mechanism 1100 from the engagement member 2220. As a result, the first stop wall 1200 does not confine the proximal ends of the clip arms 2210 anymore, and the stop blocks 2211 at the proximal ends of the clip arms 2210 enter the locking slots 2101, locking the clip head assembly 2200. It would be appreciated that, due to the presence of the second limiting member (e.g., the pin 2300 of FIG. 4, or the second step arms 2106 of FIG. 9), the clip head assembly 2200 can move substantially only along the axis of the constricting sleeve 2100 without circumferential rotation (such circumferential rotation is made impossible, for example, because the portions of the clip arms 2210 located distally with respect to the distal end of the constricting sleeve 200 abut against the tubular wall of the constricting sleeve 2100 and the second limiting member), enabling circumferential alignment of the locking slots 2101 with the stop blocks 2211, which ensures their successful connection.

Referring back to FIGS. 1 to 5, the adaptor bush assembly 3000 defines a second lumen axially extending therethrough and configured to receive the traction device therein. The adaptor bush assembly 3000 includes a sleeve 3100, and in this embodiment, a distal end of the sleeve 3100 defines an annular third limiting member 3101 radially projecting inwardly. The third limiting member 3101 is configured for mating and connection with the constricting sleeve 2100.

Figure 11:
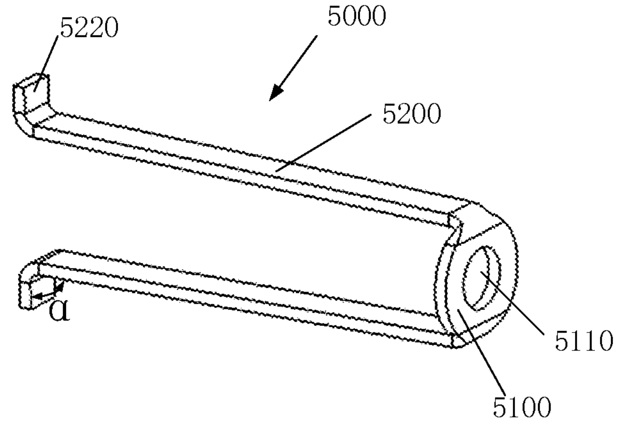
FIG. 11 is a schematic diagram showing the structure of the elastic connecting member in the hemostatic clip according to the first embodiment of the present invention.

Specifically, the hemostatic clip further includes an elastic connecting member 5000 (see FIGS. 3, 4 and 11), the elastic connecting member 5000 includes a base portion 5100 and shaft portions 5200. The base portion 5100 is disposed within the second lumen of the adaptor bush assembly 3000 and defines a through hole 5110 therein. A diameter of the through hole 5110 is greater than or equal to the outer diameter of the core wire 1110 and is smaller than the outer diameter of the coupling tube 1120. In this way, the base portion 5100 can be disposed over the outer surface of the core wire 1110 in the traction device. The shaft portions 5200 are provided on the side of the base portion 5100 closer to a distal end of the adaptor bush assembly 3000 so as to extend along the axis of the adaptor bush assembly 3000. The distal end of the shaft portions 5200 define outwardly bent fins 5220. The bent fins 5220 are bent at angles of 90°-120° (e.g., a in FIG. 11). The bent fins 5220 (radially) pass through the first connecting slots 2103 in the constricting sleeve 2100 and protrude out of the constricting sleeve 2100 so as to define stop grooves between the first step surface 2102. When the sleeve 3100 is disposed over an outer surface of the second section of the constricting sleeve 2100, the third limiting member 3101 of the sleeve 3100 is disposed in the stop grooves (i.e., the third limiting member 3101 is confined between the bent fins 5220 and the first step surface 2102), thereby coupling the adaptor bush assembly 3000 to the constricting sleeve 2100 in such a manner that the two can rotate relative to each other. With this arrangement, the bent fins 5220 may be deformed under the action of an external force to disengage from the first connecting slots 2103, thus decoupling the adaptor bush assembly 3000 from the constricting sleeve 2100.

Figure 2:
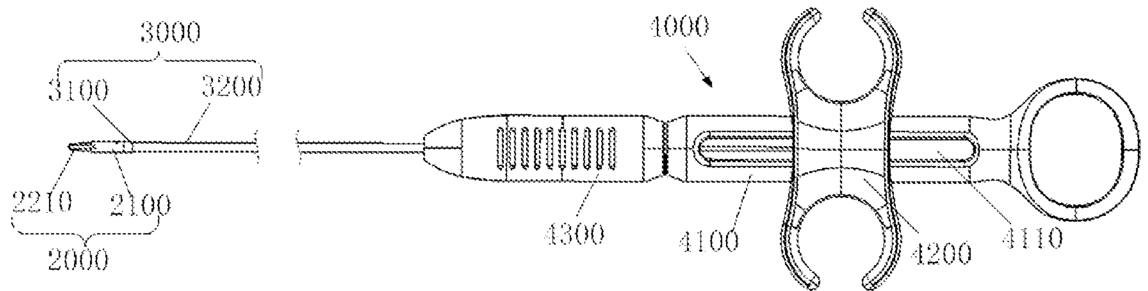
FIG. 2 is a schematic diagram showing the structure of the hemostatic clip according to the first embodiment of the present invention, in which the clip head assembly is in a closed configuration.

Further, with reference to FIGS. 1, 2 and 8, the adaptor bush assembly 3000 further includes a spring tube 3200, the distal end of the spring tube 3200 is connected to a proximal end of the sleeve 3100 and the proximal end of the spring tube 3200 is provided with a locating tube 3210. The locating tube 3210 may have a circular cross-section and is configured for connection with the handle assembly 4000.

Figure 12:
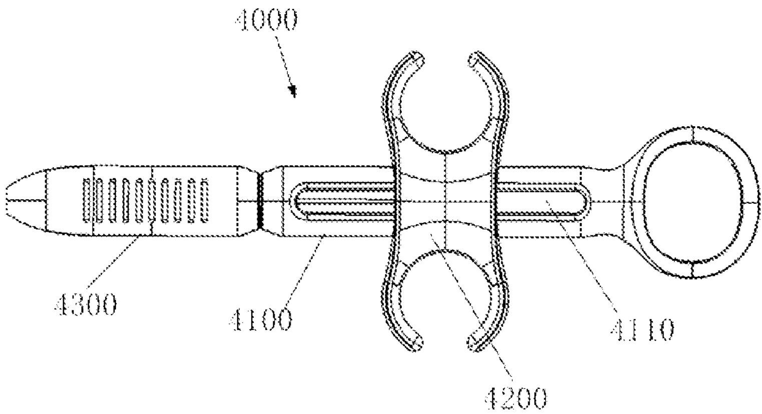
FIG. 12 is a schematic diagram showing the structure of a handle assembly in the hemostatic clip according to the first embodiment of the present invention.

With continued reference to FIGS. 1, 2 and 12, the handle assembly 4000 includes a grip member 4100, a slidable member 4200 and a rotatable member 4300. The grip member 4100 defines an axially-extending slide slot 4110, and the slidable member 4200 is coupled to the slide slot 4110 so as to be slidable within the slide slot 4110. The rotatable member 4300 is rotatably disposed at a distal end of the grip member 4100. The proximal end of the traction mechanism 1100 (more precisely, the proximal end of the core wire 1110) extends out of the proximal end of the adaptor bush assembly 3000 (so that the first connecting block 1130 is located proximally with respect to the locating tube 3210) and coupled to the slidable member 4200 and the rotatable member 4300 in the handle assembly 4000. Further, the hemostatic clip is configured so that the slidable member 4200 drives the traction mechanism 1100 to move along the axis of the adaptor bush assembly 3000 when the slidable member 4200 slides in the slide slot 4110. Furthermore, when the rotatable member 4300 rotates relative to the grip member 4100, the rotatable member 4300 drives the traction mechanism 1100 to rotate.

Figure 13:
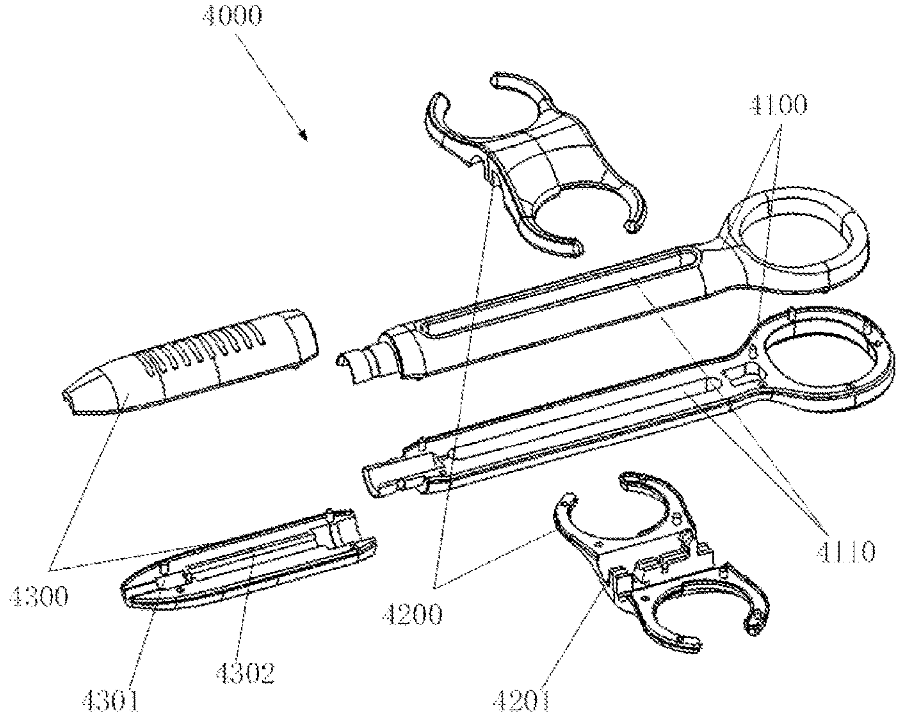
FIG. 13 is a schematic exploded view of the handle assembly in the hemostatic clip according to the first embodiment of the present invention.

With additional reference to FIG. 13, the rotatable member 4300 defines therein a first securing cavity 4301 and a second securing cavity 4302, and the slidable member 4200 defines therein a third securing cavity 4201. The first securing cavity 4301, the second securing cavity 4302 and the third securing cavity 4201 communicate with one another. Both the first securing cavity 4301 and the third securing cavity 4201 may have circular cross-sections, and the second securing cavity 4302 may have a cross-section matching that of the first connecting block 1130. The locating tube 3210 of the spring tube 3200 is disposed in the first securing cavity 4301 and configured to be axially stationary relative to the rotatable member 4300. Moreover, the rotatable member 4300 is configured to be rotatable relative to the locating tube 3210 (i.e., the locating tube 3210 is not rotatable), avoiding twisting of the adaptor bush assembly 3000 during its rotation with the traction mechanism 1100. The first connecting block 1130 of the traction mechanism 1100 is disposed in the second securing cavity 4302 and configured to be axially movable within the second securing cavity 4302 and rotatable in synchronization with the rotatable member 4300. The second locating block 1140 of the traction mechanism 1100 is disposed in the third securing cavity 4201 and configured to be axially stationary relative to the slidable member 4200 and circumferentially rotatable relative to the slidable member 4200, thereby avoiding twisting of the traction mechanism 1100 during its rotation.

In this embodiment, as shown in FIG. 13, the grip member 4100, the slidable member 4200 and the rotatable member 4300 are all preferred to be modular structures, which can facilitate assembly of the handle assembly 4000 with the traction mechanism 1100 and the adaptor bush assembly 3000.

A method of using the hemostatic clip of the present embodiment will be described below.

After the hemostatic clip is delivered to the target site in the patient's body, the operator may manipulate the handle assembly 4000 to cause the slidable member 4200 to slide (distally) within the slide slot 4110 to drive the traction mechanism 1100 to move along the axis of the adaptor bush assembly 3000. As a result, the clip head assembly 2200 is driven to move distally along the axis of the constricting sleeve 2100, thereby opening the two clip arms 2210. Moreover, the operator may manipulate the handle assembly 4000 to cause the rotatable member 4300 to rotate relative to the grip member 4100 to drive the clamping device (i.e., the clip head assembly 2200 and the constricting sleeve 2100) to rotate, thereby adjusting a position and orientation of the clip head assembly 2200 until the target tissue is located between the two clip arms 2210.

After that, the operator may apply a pulling force to the slidable member 4200 to retract the slidable member 4200. As a result, the traction mechanism 1100 drives the clip head assembly 2200 to move toward the proximal end of the constricting sleeve 2100 under a distal end face of the third connecting block 2222 in the engagement member 2220 comes into abutment against the third step surface 2104 of the constricting sleeve 2100.

Subsequently, the operator may increase the (axial) pulling force to a value greater than the first predetermined value to overcome the interference fit between the proximal end portion of the engagement member 2220 (more precisely, the proximal end portion of the second connecting shaft 2223) and the inner bore 1101 of the traction mechanism 1100, thereby separating the engagement member 2220 from the traction mechanism 1100. As a result, the first stop wall 1200 does not confine the proximal end portions of the clip arms 2210 any longer, and the stop blocks 2211 enter and engage with the locking slots 2101, locking the clip head assembly 2200.

Afterward, the operator may further retract the slidable member 4200 until the coupling tube 1120 of the traction mechanism 1100 comes into abutment against the base portion 5100 of the elastic connecting member 5000.

Next, the operator may additionally increase the pulling force (axially) to a value greater than a second predetermined value. The pulling force is transmitted by the coupling tube 1120 to the elastic connecting member 5000, causing deformation of the bent fins 5220 and disengagement thereof from the first connecting slots 2103. As a result, the adaptor bush assembly 3000 is separated from the constricting sleeve 2100. The second predetermined value may be determined as any value depending on the material of the elastic connecting member 5000, as long as a pulling force greater than the second predetermined value can cause deformation of the bent fins 5220.

Finally, the operator may further retract the slidable member 4200 to withdraw the adaptor bush assembly 3000 and the traction device 1000 from the patient's body.

Embodiment 2

Figure 14:
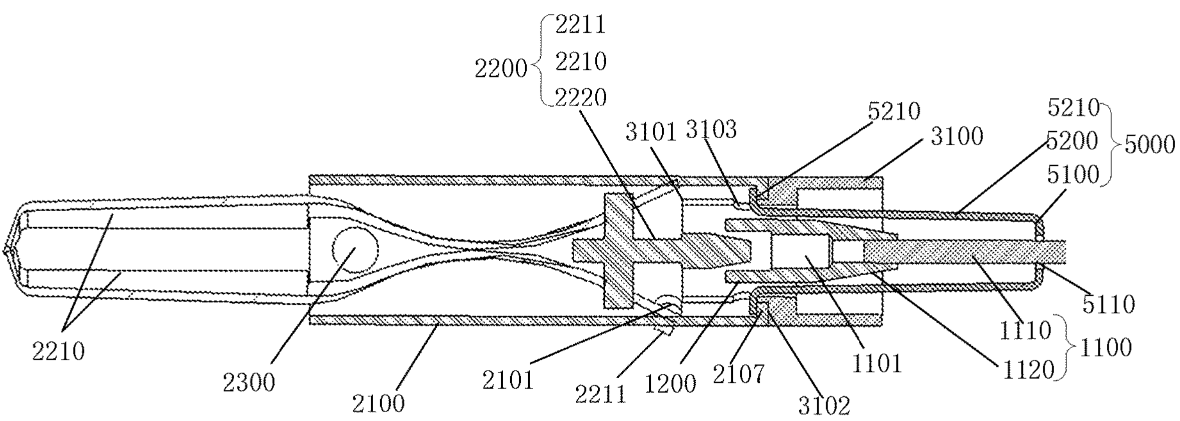
FIG. 14 is a cross-sectional view of a portion of a hemostatic clip according to a second embodiment of the present invention.
Figure 15:
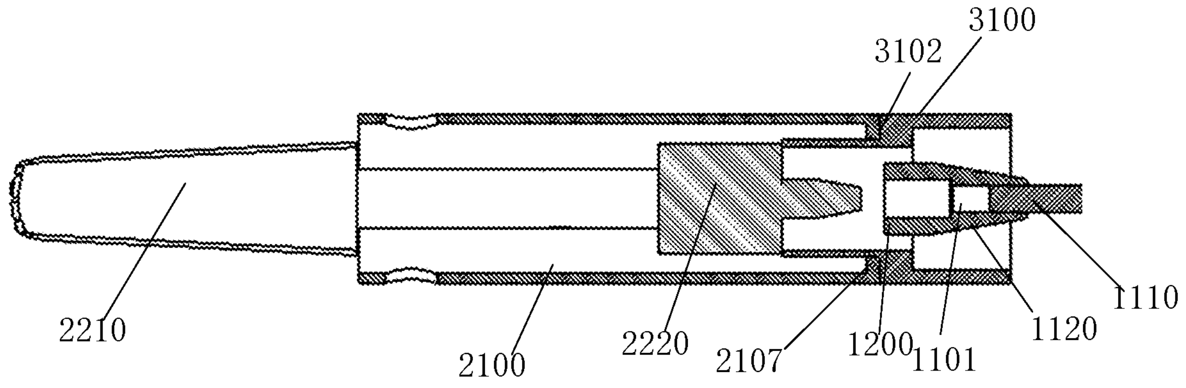
FIG. 15 is a cross-sectional view of a portion of the hemostatic clip according to the second embodiment of the present invention.

Referring to FIGS. 14 and 15, a second embodiment differs from the first embodiment in that a distal end portion of the sleeve 3100 is inserted into the first lumen of the constricting sleeve 2100 from the proximal end of the constricting sleeve 2100 and that a distal end face 3101 of the sleeve 3100 provides the second limiting surface.

Specifically, the distal end of the constricting sleeve 2100 defines a fourth limiting member 2107 radially projecting inwardly. The sleeve 3100 includes a third section and a fourth section. The third section is distal with respect to the fourth section and has an outer diameter smaller than an outer diameter of the fourth section. Thus, a second step surface 3102 is defined on an outer wall surface of the sleeve 3100. Second connecting slots 3103 are provided in the third section of the sleeve 3100 (i.e., the second connecting slots 3103 are located distally with respect to the second step surface 3102). The bent fins 5220 of the elastic connecting member 5000 pass through the second connecting slots 3103 and protrude out of the sleeve 3100. The proximal end of the constricting sleeve 2100 is disposed over an outer surface of the third section of the sleeve 3100, and the fourth limiting member 2107 is confined between the bent fins 5220 and the second step surface 3102, thereby coupling the adaptor bush assembly 3000 to the constricting sleeve 2100 in such a manner that the two can rotate relative to each other.

Similar to Embodiment 1, after the proximal end face of the third connecting block 2222 in the engagement member 2220 comes into abutment against the distal end face 3101 of the sleeve 3100, the operator may manipulate the slidable member 4200 of the handle assembly 4000 to apply a pulling force greater than the first predetermined value to the traction mechanism 1100 to separate the coupling tube 1120 from the engagement member of the clip head assembly 2220. As a result, the separation mechanism does not confine the proximal end portions of the clip arms 2210 anymore, and the stop blocks 2211 enter and engage with the locking slots 2101. Moreover, the operator may apply a pulling force greater than the second predetermined value to the traction mechanism 1100 to cause deformation of the bent fins 5220 to separate the adaptor bush assembly 3000 from the constricting sleeve 2100.

Figure 16:
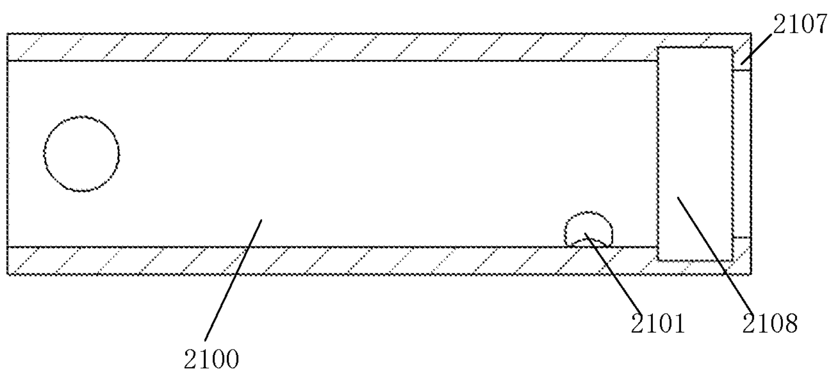
FIG. 16 is a cross-sectional view of the constricting sleeve in the hemostatic clip according to the first embodiment of the present invention.

In an optional implementation, the constricting sleeve 2100 has an inner diameter that is constant across its entire axial length, the proximal end of the constricting sleeve 2100 is provided with an annular third stop wall serving as the fourth limiting member (not shown). In another implementation, as shown in FIG. 16, an annular groove 2108 is defined in the inner wall surface of the constricting sleeve 2100 around the proximal end thereof. In this case, an inner wall surface portion of the constricting sleeve 2100 located proximally with respect to the annular groove 2108 serves as the fourth limiting member 2107.

Although the present invention has been disclosed hereinabove, it is not limited to the above disclosure. Those skilled in the art can make various changes and modifications to the invention without departing from the spirit and scope thereof. Accordingly, it is intended that any and all such changes and modifications also fall within the scope of the present invention as defined by the appended claims and equivalents thereof.

What is claimed is:

1. A hemostatic clip, comprising:

a traction device comprising a traction mechanism and a separation mechanism, a distal end of the traction mechanism defining an inner bore, the separation mechanism disposed outside of a distal end of the inner bore;

a clamping device comprising a constricting sleeve and a clip head assembly, the constricting sleeve provided thereon with a first locking member, the clip head assembly partially disposed within the constricting sleeve, the clip head assembly comprising a clip arm and an engagement member, the clip arm disposed on the engagement member, a proximal end of the clip arm provided with a second locking member for connection with the first locking member, wherein a proximal end of the engagement member is inserted in the inner bore and forms an interference fit with the inner bore, and wherein the separation mechanism prevents the second locking member from being connected to the first locking member, thereby allowing the traction mechanism to drive, under the action of an external force, the clip head assembly to move along an axis of the constricting sleeve, thereby switching the clip head assembly between a closed configuration and an opened configuration; and a first limiting member for defining a maximum distance that the clip head assembly is movable toward a proximal end of the constricting sleeve, wherein the hemostatic clip is configured so that, in the closed configuration of the clip head assembly, when the first limiting member prevents further movement of the clip head assembly toward the proximal end of the constricting sleeve and when a pulling force greater than a first predetermined value is applied to the traction mechanism, the proximal end of the engagement member is disengaged from the inner bore, and the separation mechanism does not confine the proximal end of the clip arm any longer, allowing the second locking member to be connected to the first locking member, wherein the hemostatic clip further comprises an elastic connecting member disposed between the traction device and the clamping device, the elastic connecting member comprising a base portion and a shaft portion, the shaft portion extending along the axis of the constricting sleeve, a distal end of the shaft portion defining a bent fin bent at an angle of 90°-120°, wherein the bent fin is configured to radially pass through a first connecting slot in the constricting sleeve and deform under a pulling force greater than a second predetermined value to allow separation of the traction device from the clamping device without fracture.

2. The hemostatic clip of claim 1, wherein the separation mechanism comprises first stop walls, which extend along an axis of the traction mechanism, the number of the first stop walls are two, the two first stop walls are arranged in circumferential symmetry with respect to the inner bore and configured to confine the proximal end of the clip arm on internal sides of the first stop walls, thereby preventing the second locking member from being connected to the first locking member.

3. The hemostatic clip of claim 1, wherein the clamping device further comprises a second limiting member, which is provided on the constricting sleeve on a distal side of the engagement member and is configured to define a maximum distance that the clip head assembly is movable away from the proximal end of the constricting sleeve, thereby preventing the clip head assembly from distal dislodgement from the constricting sleeve.

4. The hemostatic clip of claim 3, wherein the first locking member comprises a locking slot provided in a tubular wall of the constricting sleeve and the second locking member comprises a stop block, wherein the second limiting member is further configured to limit circumferential relative positions of the clip head assembly and the constricting sleeve to enable the stop block to enter and engage with the locking slot after the confinement is removed.

5. The hemostatic clip of claim 4, wherein the second limiting member extends radially with respect to the constricting sleeve and delimits two channels together with the tubular wall of the constricting sleeve, wherein two clip arms are provided, a distal end of one of the clip arms protruding through a respective one of the channels to extend out of the distal end of the constricting sleeve.

6. The hemostatic clip of claim 5, wherein the second limiting member comprises a pin; or wherein the second limiting member comprises two second stop walls provided at the distal end of the constricting sleeve, the two second stop walls arranged in circumferential symmetry with respect to the constricting sleeve.

7. The hemostatic clip of claim 4, further comprising an adaptor bush assembly, which is detachably coupled to the proximal end of the constricting sleeve and communicates with the constricting sleeve, and the adaptor bush assembly configured to be rotatable relative to the constricting sleeve, wherein the traction device is partially disposed in the adaptor bush assembly and is movable along an axis of the adaptor bush assembly, and wherein the hemostatic clip is configured so that the traction mechanism is able to drive, under the action of an external force, rotation of the clip head assembly about an axis of the traction mechanism and rotation of the constricting sleeve about its own axis.

8. The hemostatic clip of claim 7, wherein the first limiting member comprises a first limiting surface and a second limiting surface, the first limiting surface provided on the engagement member and configured to abut against the second limiting surface, wherein a first step surface is defined on an outer wall surface of the constricting sleeve, and the second limiting surface is formed on an inner wall surface of the constricting sleeve, wherein the constricting sleeve is further provided therein with the first connecting slot, the first connecting slot located proximally with respect to the first step surface and the second limiting surface, wherein the base portion disposed within the adaptor bush assembly and provided therein with a through hole for passage of the traction mechanism therethrough, the shaft portion disposed on a side of the base portion closer to a distal end of the adaptor bush assembly and extending along the axis of the adaptor bush assembly, wherein the distal end of the adaptor bush assembly defines an inwardly-projecting third limiting member, and wherein the distal end of the adaptor bush assembly is disposed over the outer surface of the proximal end of the constricting sleeve, the third limiting member is confined between the bent fin and the first step surface.

9. The hemostatic clip of claim 8, wherein the traction mechanism comprises a core wire and a coupling tube, the core wire passing through the through hole in the base portion, the coupling tube disposed at a distal end of the core wire, the coupling tube defining the inner bore, a proximal end of the coupling tube having an outer diameter that is greater than a diameter of the through hole, wherein the hemostatic clip is configured so that, after the proximal end of the engagement member is disengaged from the inner bore, when the proximal end of the coupling tube abuts against the base portion and when the pulling force greater than the second predetermined value is applied to the traction mechanism, the bent fin deforms so that the adaptor bush assembly is separated from the constricting sleeve.

10. The hemostatic clip of claim 7, wherein the first limiting member comprises a first limiting surface and a second limiting surface, the first limiting surface provided on the engagement member and configured to abut against the second limiting surface, wherein an outer wall surface of a distal end of the adaptor bush assembly is provided with a second step surface, wherein the adaptor bush assembly is further provided therein with the second connecting slot, the second connecting slot located distally with respect to the second step surface, wherein the base portion disposed within the adaptor bush assembly and provided therein with a through hole for passage of the traction mechanism therethrough, the shaft portion disposed on a side of the base portion closer to the distal end of the adaptor bush assembly and extending along the axis of the adaptor bush assembly, wherein the proximal end of the constricting sleeve defines an inwardly-projecting fourth limiting member, and wherein the proximal end of the constricting sleeve is disposed over the outer surface of the distal end of the adaptor bush assembly, the fourth limiting member is confined between the bent fin and the second step surface; and a distal end face of the adaptor bush assembly makes up the second limiting surface for abutting against the first limiting surface.

11. The hemostatic clip of claim 10, wherein the traction mechanism comprises a core wire and a coupling tube, the core wire passing through the through hole in the base portion, the coupling tube disposed at a distal end of the core wire, the coupling tube defining the inner bore, a proximal end of the coupling tube having an outer diameter that is greater than a diameter of the through hole, wherein the hemostatic clip is configured so that, after the proximal end of the engagement member is disengaged from the inner bore, when the proximal end of the coupling tube abuts against the base portion and when the pulling force greater than the second predetermined value is applied to the traction mechanism, the bent fin deforms so that the adaptor bush assembly is separated from the constricting sleeve.

12. The hemostatic clip of claim 7, further comprising a handle assembly, the handle assembly comprising a grip member, a slidable member and a rotatable member, the grip member defining an axially-extending slide slot, the slidable member disposed in the slide slot and is slidable in the slide slot, the rotatable member rotatably disposed at a distal end of the grip member, wherein the proximal end of the traction mechanism extends out of a proximal end of the adaptor bush assembly into the handle assembly, thereby connecting to both the slidable member and the rotatable member of the handle assembly, and wherein the hemostatic clip is configured so that the slidable member drives, when sliding in the slide slot, the traction mechanism to move along the axis of the adaptor bush assembly to cause the clip head assembly to move along the axis of the constricting sleeve and that the rotatable member drives, when rotating relative to the grip member, the traction mechanism to rotate about its own axis to cause rotation of the clip head assembly and the constricting sleeve.

13. The hemostatic clip of claim 12, wherein the traction mechanism comprises a core wire, a coupling tube, a first connecting block and a second connecting block, the coupling tube disposed at a distal end of the core wire and defining the inner bore, the first connecting block and the second connecting block both disposed over a proximal end of the core wire, the second connecting block located proximally with respect to the first connecting block, the first connecting block coupled to the rotatable member and configured to be rotatable in synchronization with the rotatable member and axially movable relative to the rotatable member, the second connecting block coupled to the slidable member and configured to be axially stationary relative to the slidable member and circumferentially rotatable relative to the slidable member, and/or the adaptor bush assembly comprises a sleeve and a spring tube, which are axially connected to each other, a distal end of the sleeve connected to the proximal end of the constricting sleeve, a proximal end of the spring tube provided with a locating tube, the locating tube located distally with respect to the first connecting block, the locating tube coupled to the rotatable member in the handle assembly, the locating tube configured to be axially stationary relative to the rotatable member and circumferentially rotatable relative to the rotatable member.

* * * * *